US010436780B2

(12) United States Patent
Ndukaife et al.

(10) Patent No.: US 10,436,780 B2
(45) Date of Patent: Oct. 8, 2019

(54) MULTI-SITE PARTICLE SENSING SYSTEM

(71) Applicant: Purdue Research Foundation, West Lafayette, IN (US)

(72) Inventors: Justus C. Ndukaife, West Lafayette, IN (US); Alexander V. Kildishev, West Lafayette, IN (US); Agbai (George) A. Nnanna, Crown Point, IN (US); Alexandra Boltasseva, West Lafayette, IN (US); Vladimir M. Shalaev, West Lafayette, IN (US); Steven Truitt Wereley, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 356 days.

(21) Appl. No.: 15/174,990

(22) Filed: Jun. 6, 2016

(65) Prior Publication Data

US 2017/0003283 A1 Jan. 5, 2017

Related U.S. Application Data

(60) Provisional application No. 62/170,718, filed on Jun. 4, 2015.

(51) Int. Cl.
*G01N 33/543* (2006.01)
*G02B 5/00* (2006.01)
*G01N 1/40* (2006.01)
*G01N 21/65* (2006.01)
*G01N 15/10* (2006.01)
(Continued)

(52) U.S. Cl.
CPC ......... *G01N 33/54373* (2013.01); *G01N 1/40* (2013.01); *G01N 15/10* (2013.01);
(Continued)

(58) Field of Classification Search
CPC .. G01N 33/54373; G01N 15/10; G01N 27/00; G01N 1/40; G02B 5/008; B03C 5/00; B01L 3/502761
See application file for complete search history.

(56) References Cited

U.S. PATENT DOCUMENTS

2008/0213821 A1* 9/2008 Liu .................. B01L 3/502761
435/39
2010/0078546 A1* 4/2010 Kyoung ............... G01N 21/553
250/225

(Continued)

OTHER PUBLICATIONS

Kinsey, N., "Examining nanophotonics for integrated hybrid systems: a review of plasmonic interconnects and modulators using traditional and alternative materials," Journal of the Optical Society of America B, 2015, 32 (1), 121-142.

(Continued)

*Primary Examiner* — Melanie Brown
(74) *Attorney, Agent, or Firm* — Purdue Research Foundation

(57) ABSTRACT

A particle sensing system which includes a plurality of micro-lenses which focus light from an unfocused or loosely focused light source onto a corresponding plurality of focus regions on a surface containing plasmonic structures. The absorption of light by the plasmonic structures in the focus regions results in heat dissipation in the plasmonic structures and consequently increases surface temperature in the focus regions. When an electrical field is applied to a sample fluid in contact with the surface, multiple electrothermal flows are induced in the fluid which rapidly transport suspended particles to the focus regions on the surface. The particles can then be captured and/or sensed.

18 Claims, 3 Drawing Sheets

(51) Int. Cl.
*B01L 3/00* (2006.01)
*G01N 15/00* (2006.01)
*B03C 5/00* (2006.01)

(52) U.S. Cl.
CPC ........... *G01N 21/658* (2013.01); *G02B 5/008* (2013.01); *B01L 3/502761* (2013.01); *B03C 5/00* (2013.01); *G01N 2001/4038* (2013.01); *G01N 2015/0019* (2013.01); *G01N 2015/0065* (2013.01)

(56) References Cited

U.S. PATENT DOCUMENTS

2011/0080329 A1* 4/2011 Nagel ................... H01Q 9/005
343/770

2012/0326256 A1* 12/2012 Salsman ........... H01L 27/14603
257/432

OTHER PUBLICATIONS

Ndukaife, J., "Photothermal Heating Enabled by Plasmonic Nanostructures for Electrokinetic Manipulation and Sorting of Particles," American Chemical Society Nano, 2014, 8 (9), 9035-9043.

Liu, J., "Optical absorption of hyperbolic metamaterial with stochastic surfaces," Optics Express, 2014, 22 (80), 8893-8901.

Lin, D., "Dielectric gradient metasurface optical elements", Applied Optics, 2014, 345, 298-302.

Acimovic, S., "LSPR Chip for Parallel, Rapid, and Sensitive Detection of Cancer Markers in Serum", NANO Letters, 2014, 14, 2636-2641.

* cited by examiner

MULTI-SITE PARTICLE SENSING SYSTEM

CROSS-REFERENCE TO RELATED APPLICATIONS

The present patent application is related to and claims the priority benefit of U.S. Provisional Patent Application Ser. No. 62/170,718, filed Jun. 4, 2015, the contents of which is hereby incorporated by reference in its entirety into this disclosure.

TECHNICAL FIELD

The present application relates to particle trapping and sensing systems, and more specifically, to systems which sense or trap particles within a liquid solution.

BACKGROUND

Various systems are known which allow isolating or sensing of particle or analyte concentration within a liquid solution. Such systems are used in many applications, such as sensing water quality or the presence of contaminants in biological samples. One prior art approach utilizes holographic optical tweezers in which a high power laser beam is split into several separate beams, with each beam having a fraction of the total power. The beams are then used to attract or repel particles of a certain type. However the throughput for such an approach is unacceptably low and the system is very costly due to the expense of adequate high power laser sources. Therefore, improvements are needed in the field.

SUMMARY

The present disclosure provides a particle sensing system which includes a plurality of micro-lenses which focus light from an unfocused or loosely focused light source onto a corresponding plurality of focus regions on a surface containing plasmonic structures. The absorption of light by the plasmonic structures in the focus regions results in heat dissipation in the plasmonic structures and consequently increases surface temperature in the focus regions. When an electrical field is applied to a sample fluid in contact with the surface, multiple electrothermal flows are induced in the fluid which rapidly transport suspended particles to the focus regions on the surface. The particles can then be captured and/or sensed. Because there are hundreds or even thousands of trapping sites (focus regions) on a single device, throughput is vastly increased when compared to prior art systems. The required power is also reduced, as the device may be activated by a low power and inexpensive light source.

According to one aspect, a particle sensing system is provided, comprising a first substrate having a first conductive layer on a first side of the first substrate, and a plurality of microlenses mounted to the first conductive layer. A second substrate having a second conductive layer faces the first conductive layer, with the second conductive layer having a plurality of light absorbing plasmonic structures. At least one channel separates the first and second conductive layers and configured to hold a liquid sample. The microlenses are configured to create a plurality of focus regions on the second conductive layer when light is directed through the microlenses.

According to another aspect, a particle sensing system is provided, comprising a first substrate having a first conductive layer on a first side of the first substrate, and a plurality of microlenses mounted to a second side of the substrate, with the first conductive layer having a plurality of light absorbing plasmonic structures. A second substrate having a second conductive layer faces the first conductive layer. At least one channel separates the first and second conductive layers and is configured to hold a liquid sample. The microlenses are configured to create a plurality of focus regions on the first conductive layer when light is directed through the microlenses, through the substrate and onto the first conductive layer.

According to another aspect, a method of concentrating particles in a liquid sample is provided, comprising directing light through a plurality of microlenses to create a corresponding plurality of focus regions on a first conductive layer of a first substrate, with the first conductive layer comprising a plurality of plasmonic structures; and applying a voltage across the first conductive layer and a second conductive layer of a second substrate, the first and second conductive layers separated by a channel containing the liquid sample, with the voltage selected to cause a predetermined particle type to be attracted to the plasmonic structures in the focus regions.

BRIEF DESCRIPTION OF THE DRAWINGS

In the following description and drawings, identical reference numerals have been used, where possible, to designate identical features that are common to the drawings.

Figure 1:
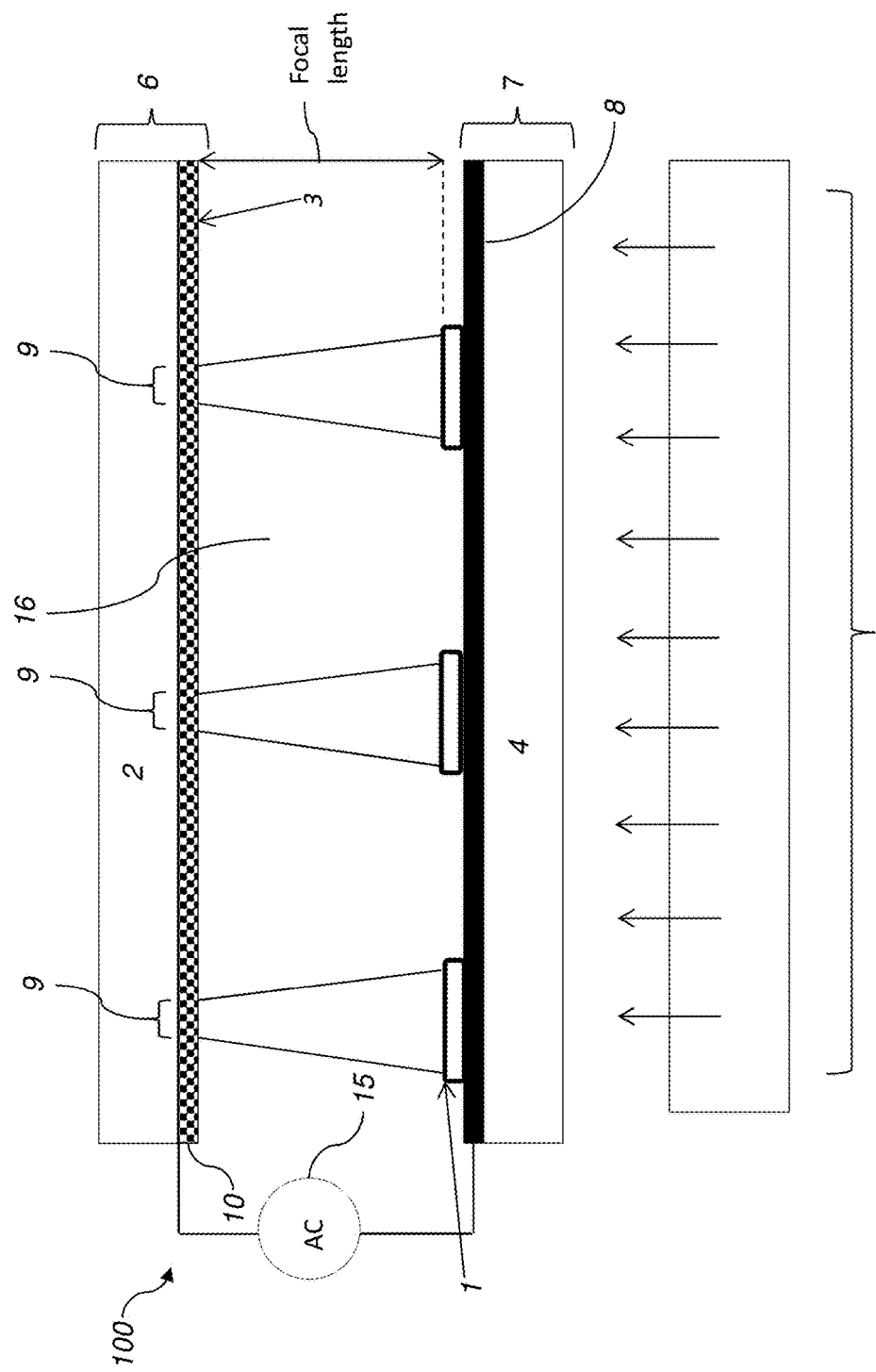
FIG. 1 is a side-view schematic diagram of a particle sensing system utilizing microlenses according to one embodiment.

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 shows a side view of a sensing system 100 according to one embodiment. The system 100 may be implemented as a lab-on-a-chip device, although other forms may be used. As shown, the system 100 includes a first substrate 4 which has an electrically conducting layer 8 (collectively indicated as member 7) attached on an upper side as shown. In one embodiment, microlenses 1 are attached to the conducting layer 8. However, the microlenses 1 may alternatively be mounted on a dielectric layer which is deposited on the electrically conductive layer 8, with the dielectric layer separating the conductive layer 8 and the microlenses 1. A second substrate 2 also has a conducting layer 10 (collectively indicated as member 6) mounted to a bottom side facing the microlenses 1. In certain embodiments, the conducting layer 10 may comprise both an electrically conducting layer and layer comprising an array of plasmonic nanostructures. The distance between the faces of the microlenses 1 and the bottom surface 3 of the conducting layer 10 is preferably chosen to be the focal length of the microlenses 1. An alternating current (AC) source 15 is connected to the conducting layers 8 and 10 as shown.

The first and second substrates 4 and 2 may comprise a material through which light can pass, such as glass or sapphire, to allow light from the source 5 to be directed through the microlenses 1. The conductive layers 8 and 10 may comprise an electrically conductive material, such as metal or metal alloy.

The microlenses 1 may comprise planar metasurface lens or dielectric solid immersion microlenses. Other lens forms may also be used. An unfocussed or collimated light source 5 projects light through the microlenses 1 and focuses the light as spots onto multiple regions 9 as shown. The light source 5 may comprise a common low power source, such as a laser pointer, table lamp, or the like.

The regions 9 contain plasmonic components and are formed as arrays of plasmonic nanostructures, continuous metal film, or a combination of both. Because the conducting layer 10 is positioned at a distance from the microlenses 1 which is approximately equal to the focal length of the microlenses 1, the focused light on the plasmonic components in the regions 9 are heated to form hotspots (each region 9 becomes a hotspot). The number of microlenses 1 in the path of the light source 5 will determine the number of corresponding hotspots (regions 9) created, assuming the regions 9 are spaced sufficiently far apart.

In certain embodiments, the plasmonic components in the regions 9 may comprise resonant plasmonic components, which will increase the heating effect due to efficient absorption and through the enhanced focusing of light at the regions 9.

When the regions 9 are heated due to the absorption of focused light to form hotspots, the plasmonic components therein would transfer heat energy to the adjoining fluid medium 16 creating temperature gradients in the fluid 16. The temperature gradients also result in a gradient in the fluid 16 electrical conductivity and permittivity. This in turn creates a net charge density in the fluid. An AC field is then applied by source 15 to cause electrothermal flow in the fluid. According to one embodiment, the AC electric field frequency chosen to below a critical frequency at which suspended particles in the fluid 16 will be attracted to and become trapped on the surface of the plasmonic components in the regions 9. In certain embodiments, the AC electric field frequency is chosen to be in the range of 1 KHz to 200 KHz, although other frequencies may be used.

Furthermore, in certain embodiments, the temperature gradient established in the adjoining fluid medium can induce gradients in the density of the fluid to produce buoyancy-driven fluid convection. Even while the AC field and light illumination are ON, both the electrothermal flow and buoyancy-driven fluid convection will be superimposed. Thus, as the AC field is turned OFF, the agglomerated particles can still remain trapped while the laser illumination is ON due to the induced buoyancy-driven convection and thermophoresis. The trapped particles may be released by also turning OFF the light illumination.

In certain embodiments, the light focused by the microlenses 1 and absorbed by the plasmonic nanostructures at the focused regions 9 results in temperature gradients. The induced temperature gradients induces buoyancy-driven convection and thermophoresis for assembly of particles at multiple sites where the light spots have been focused.

Because there are hundreds or thousands of microlenses 1 in the path of the light source 5, a corresponding number of trapping sites (regions 9) are created. Therefore, integrating microlenses 1 to cover the area over which the sample fluid 16 is present enables trapping of nearly all particles suspended in the fluid, even at very low concentrations.

In addition to serving as particle gathering or trapping sites, the plasmonic components in the regions 9 also serves as a sensing substrate for detection of the analyte. The disclosed embodiment therefore provides a self-contained system for both on-chip concentrating, sorting, and sensing of particles or analytes.

Figure 2:
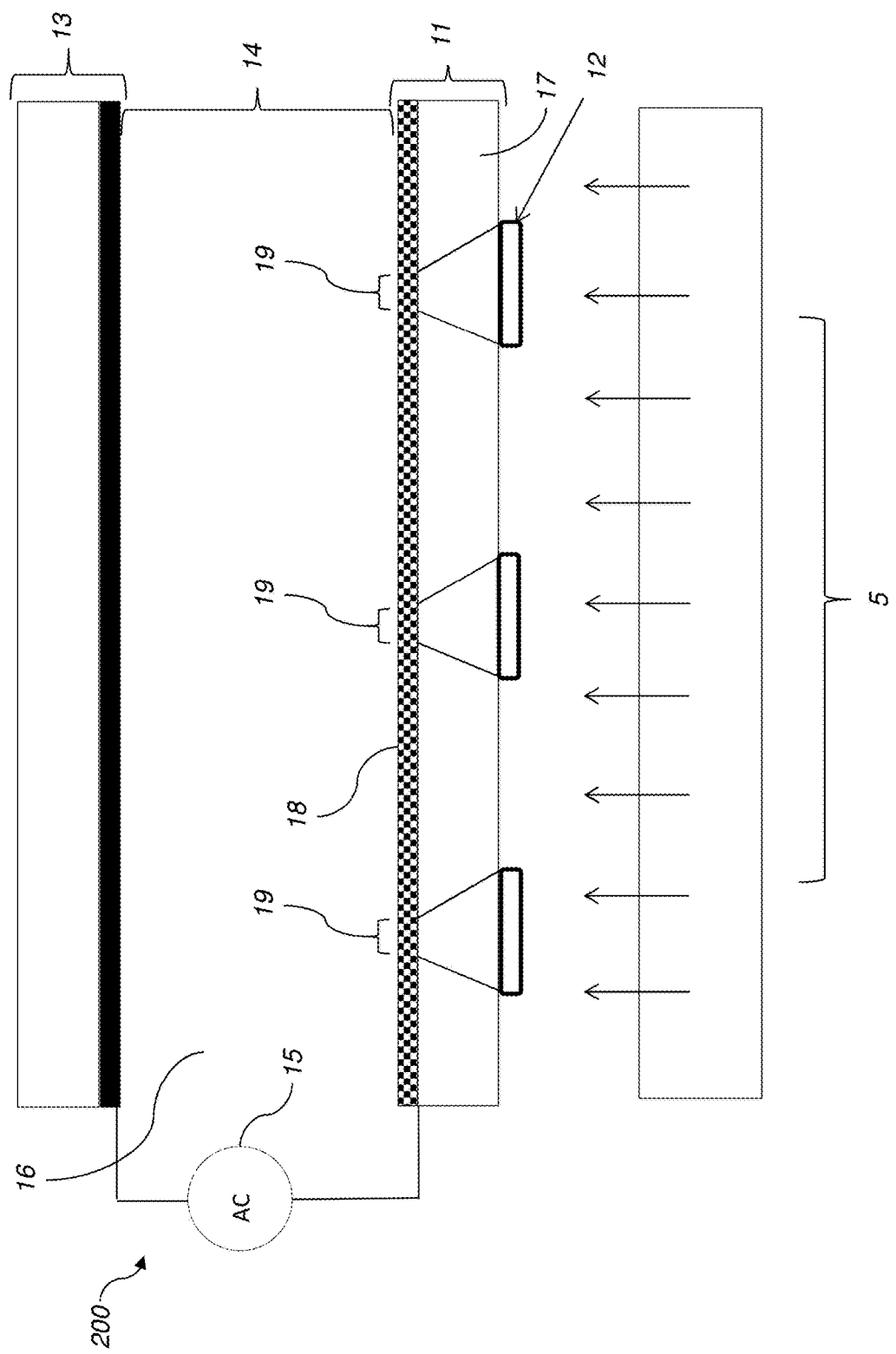
FIG. 2 is a side-view schematic diagram of a particle sensing system utilizing microlenses according to another embodiment.

FIG. 2 shows a sensing system 200 according to another embodiment. The system 200 is similar to system 100, but has microlenses 12 mounted on an outer or bottom side of the first substrate 17 as shown. The conducting layer 18 is similar to conducting layer 10 and similarly comprises a plurality of plasmonic structures. The second substrate/conducting layer 13 is similar to substrate/conducting layer 7, with the sample fluid situated between the layer 13 and layer 18. In the embodiment of FIG. 2, the light source 5 is directed through the microlenses 12, through the substrate 17, and onto the regions 19 in the conducting layer 18. The plasmonic structures in the regions 19 of the conducting layer 18 become hotspots and thereby create thermal gradients and particle trapping sites as described above with respect to system 100. The plasmonic structures may also be separated from the conducting layer 18 by a dielecric layer.

Figure 3:
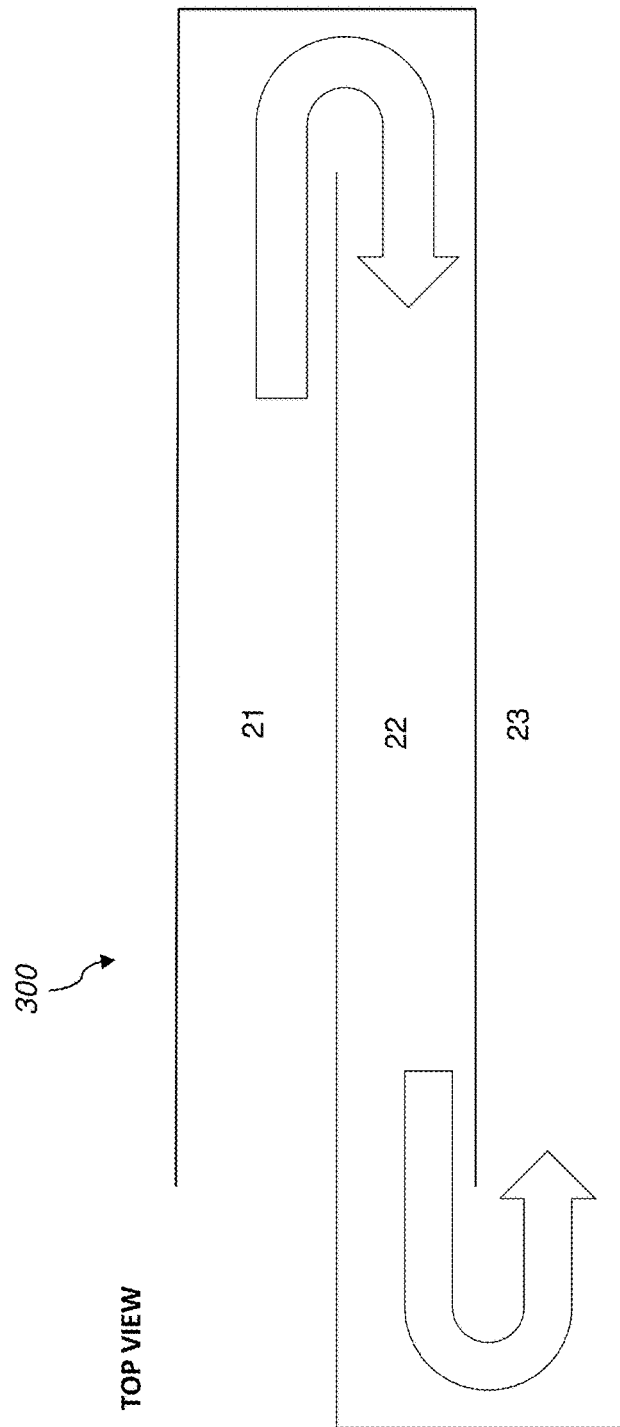
FIG. 3 is a top-view schematic diagram of microchannels through which a sample solution is directed according to one embodiment.

In further embodiments, the system 100 or 200 may be used to separate particles of different sizes or types from the liquid sample. FIG. 3 shows a top view of one embodiment wherein a separation structure comprising a plurality of channels 21, 22, 23 is provided. Each channel includes a system 100 or 200 therein to form hotspots within the channel for trapping particles from the sample. The sample is first directed through channel 21, with the AC source 15 frequency set to trap particles of a first size (e.g., the smaller particles) at the hotspots contained within the channel 21.

In certain embodiments, the plasmonic components array on which the particles are concentrated in channel 21 may be functionalized to bind the concentrated target particles. For example, in embodiments wherein the concentrated particles are analytes, the plasmonic nanostructures may be functionalized with antibodies that can selectively bind to the target concentrated analyte. Other bio-molecules such as aptamers can also be used to functionalize the plasmonic nanostructure array to bind concentrated particles such as DNA molecules to the plasmonic nanostructure array.

After passing through channel 21, the sample is then directed through channel 22 as indicated by the arrows and the AC source 15 frequency is adjusted to trap a second size of particles from the sample. The sample is then directed to channel 23 and the AC signal source is again adjusted to trap a third particle size. The process may be repeated with additional channels until all desired particles of interest have been trapped.

In a further embodiment, the plasmonic components in the conductive layer 10 or 18 may be selectively coated with polymers (e.g., loaded with biomolecules for selective functionalization) to change their local dielectric environment and resonance properties. For example, a solution containing polymer particles may be added to the above systems 100 or 200. By applying a DC voltage (e.g., 5 volts) across the conducting layers 10 or 18, the polymer particles will permanently stick to the plasmonic structures in the hotspots (regions 9 or 19). This is because particles in a fluid acquire an electrical double layer (layer of charge surrounding it that screens their surface charge). DC field causes a Faradaic reaction that results in the collapse of the electrical double layer as well as exerts a force on the particle drawing them closer to the electrode surface. As they are brought closer to the surface, short range interactions such as van der Waals can then kick in to hold them on the surface. The chip (system 100 OR 200) is then placed in an oven or otherwise heated to a few degrees above room temperature (e.g., less than ten degrees Celsius above room temperature), causing the polymer particles to expand and coat the plasmonic structures. If the polymer particles are loaded with biomolecules, the biomolecules will be released to selectively functionalize those specific regions. Furthermore, in another embodiment, selective tuning of resonance of the plasmonic systems can be achieved by capturing polymers of different optical properties, and heating them to coat the selected nanoantennas, thereby changing their dielectric environment and hence resonance spectrum. This can be used to achieve color printing with the plasmonic nanoantennas.

After being gathered or trapped using the above system, the particles may be sensed, imaged, or otherwise evaluated. In certain embodiments, the same light source 5 may be used to both create the hotspots in the focus regions and sense or image the particles. The light source 5 may also be optionally shaped or patterned to illuminate a selected subset of the microlenses 1. In certain embodiments, the light source 5 may be polarized to focus light with a selected subset of the lenses, with the corresponding subset of lenses being polarization sensitive. For example, a first subset of the micro lenses may be configured to focus the selected polarization onto the plasmonic components array with a different functionalization for binding the concentrated target particles than a second subset of the micro lenses.

Steps of various methods described herein can be performed in any order except when otherwise specified, or when data from an earlier step is used in a later step. Exemplary method(s) described herein are not limited to being carried out by components particularly identified in discussions of those methods.

The invention is inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless otherwise explicitly noted. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected within the spirit and scope of the invention.

The invention claimed is:

1. A particle sensing system, comprising:
   a first substrate having a first conductive layer on a first side of the first substrate, and a plurality of microlenses mounted to the first conductive layer;
   a second substrate having a second conductive layer, the second conducting layer facing the first conductive layer, the second conductive layer having a plurality of light absorbing plasmonic structures; and
   at least one channel separating the first and second conductive layers and configured to hold a liquid sample;
   wherein the microlenses are configured to create a plurality of focus regions on the second conductive layer when light is directed through the microlenses.

2. The system of claim 1, further comprising an alternating current (AC) source connected between the first and second conductive layers to induce an electric field in the liquid sample.

3. The system of claim 1, wherein the distance between the microlenses and the second conductive layer is chosen to be equal to a focal length of the microlenses.

4. The system of claim 1, wherein the plurality of microlenses are arranged in arrays on the first conductive layer.

5. The system of claim 1, wherein a thin dielectric spacer layer is placed between the microlenses and the first conductive layer.

6. The system of claim 1, wherein the first conductive layer functions as the array of microlenses.

7. The system of claim 1, wherein the microlenses are fabricated by patterning the first conductive layer.

8. The system of claim 1, wherein the plasmonic structures comprise nanoholes, nanostructures, or a planar thin film.

9. The system of claim 1, further comprising a light source configured to direct unfocused light through the microlenses and create the focus regions on the second conductive layer having the plasmonic nanostructures.

10. The system of claim 1, wherein the light source is also used to image the particles.

11. The system of claim 1, wherein the light source is shaped or patterned to selectively direct light to only a subset of the microlenses.

12. The system of claim 1, wherein the light source has a selected polarization, and wherein a first subset of the micro lenses may be configured to focus the selected polarization onto the plasmonic components array with a different functionalization for binding the concentrated target particles than a second subset of the micro lenses.

13. The system of claim 1, wherein the light source is directed to the microlenses at an angle and the light reflected by the microlenses is directed to the second conductive layer.

14. The system of claim 1, wherein the second conductive layer comprises a metamaterial having a repeating pattern of plasmonic structures.

15. The system of claim 1, wherein the at least one channel comprises a non-conducting material and positioned to separate the first and second substrate, the separation having a height of less than 300 microns, the microchannel comprising a groove to hold liquid particles.

16. The system of claim 1, wherein the at least one channel comprises a plurality of microchannels configured to hold the liquid sample, the microchannels configured to allow the liquid sample to be directed through the microchannels in an ordered fashion.

17. The system of claim 1, wherein the microlenses and the second conductive layer are configured to heat the focus regions and create thermal gradients in the liquid sample.

18. The system of claim 1, wherein the plasmonic structures are configured to attract particles of a predetermined type from the liquid sample when a voltage signal of a given frequency is applied across the first and second conducting layers.

* * * * *